United States Patent [19]

Lever, Jr. et al.

[11] Patent Number: 4,871,865

[45] Date of Patent: Oct. 3, 1989

[54] TRICYCLIC AROMATIC COMPOUNDS

[75] Inventors: O. William Lever, Jr., Skillman, N.J.; Harry J. Leighton, Chapel Hill, N.C.

[73] Assignee: Burroughs Wellcome Co., Research Triangle Park, N.C.

[21] Appl. No.: 894,306

[22] Filed: Aug. 7, 1986

[30] Foreign Application Priority Data

Aug. 17, 1985 [GB] United Kingdom ............... 8520662

[51] Int. Cl.$^4$ .................. C07D 313/12; C07C 87/459
[52] U.S. Cl. .................................... 549/354; 562/442
[58] Field of Search .......................................... 549/354

[56] References Cited

U.S. PATENT DOCUMENTS

| | | | |
|---|---|---|---|
| 2,905,668 | 9/1959 | Jacob et al. | 260/243 |
| 3,401,192 | 9/1968 | Kollonitsch et al. | |
| 3,420,851 | 1/1969 | Bloom et al. | 549/354 |
| 3,509,175 | 4/1970 | Tretter | 260/333 |
| 4,223,013 | 9/1980 | Hu et al. | 435/188 |
| 4,282,365 | 8/1981 | Rokach et al. | 548/252 |
| 4,307,245 | 12/1981 | Hu et al. | 562/442 |

FOREIGN PATENT DOCUMENTS

| | | |
|---|---|---|
| 37254 | 10/1981 | European Pat. Off. |
| 92114 | 10/1983 | European Pat. Off. |
| 130555 | 1/1985 | European Pat. Off. |
| 1018995 | 2/1966 | United Kingdom |
| 1412095 | 10/1975 | United Kingdom |

OTHER PUBLICATIONS

B. A. Patel et al., J. Org. Chem., vol. 42(24) (1977), pp. 3903–3907.

M. Leitold et al., Arzneim.-Forsch./Drug. Res. 34(1), No. 4, (1984), pp. 468–473.
C. A. Stone et al., J. Med. Chem., vol. 8 (1965), pp. 829–835.
Wilson et al., Textbook of Organic Medicinal and Pharmaceutical Chemistry, 3rd ed. (1956), J. B. Lippincott Co., pp. 374–376.
Stedman's Medical Dictionary, 23rd ed. (1976), p. 648.
Remington's Pharmaceutical Sciences, 14th ed. (1970), Mack Publ. Co., pp. 1142–1144, 1152–1153.

*Primary Examiner*—Richard L. Raymond
*Assistant Examiner*—Ba Trinh
*Attorney, Agent, or Firm*—Donald Brown

[57] ABSTRACT

The present invention relates to compounds of formula I

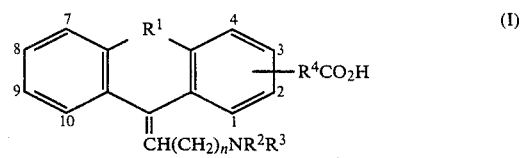

or a salt, ester or amide thereof; wherein $R^1$ is —CH$_2$—CH$_2$—, CH$_2$—O— or —O—CH$_2$—; $R^2$ and $R^3$ are the same or different and are each hydrogen, C$_{1-4}$ alkyl or taken together with the nitrogen comprise a nitrogen-containing heterocyclic ring having four to six ring members; $R^4$ is a single bond or a C$_{1-7}$ bivalent aliphatic hydrocarbon group and may be joined to the aromatic ring system at the 2,3,8 or 9 positions; n is 0 to 3, and their use as anithistamine and antiasthma agents.

3 Claims, No Drawings

TRICYCLIC AROMATIC COMPOUNDS

The present invention relates to new chemical compounds which have potent antihistaminic activity, to processes for preparing them and to their use in medicine. Belg. Patent 623259, Neth. Patent Appl. 6407758, Neth, Patent Appl. 6411861 and Belg. Patent 641498 disclose a group of 11-[(dialkylamino)alkylidene]-6,11-dihydrodibenz[b,e]oxepins as psychotherapeutic agents the most outstanding of which is the compound named, (11-(3-(dimethylamino)propylidene)-6,11-dihydrodibenz[b,e]oxepin), and hereinafter referred to by its generic name, doxepin. Doxepin has been accepted as an antidepressant in human clinical chemotherapy and an antipruritic for veterinary use. We have now discovered that a group of carboxylic acid derivatives of doxepin possess surprisingly potent antihistaminic and anti-asthmatic properties. In this invention, compound (Z)-11-(3-(dimethylamino)propylidene)-6,11-dihydrodibenz[b,e]oxepin-2-carboxylic acid exhibits extremely good antihistaminic activity in vivo.

Accordingly this invention provides a compound of the formula (I),

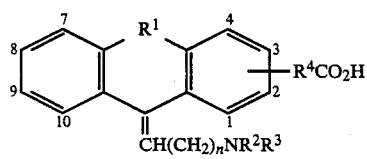

(I)

or a salt, ester or amide thereof; wherein $R^1$ is —$CH_2$—$CH_2$—, —$CH_2$—O— or —O—$CH_2$—;

$R^2$ and $R^3$ are the same or different and are each hydrogen, $C_{1-4}$ alkyl or taken together with the nitrogen comprise a nitrogen-containing heterocyclic ring having four to six ring members;

$R^4$ is a single bond or a $C_{1-7}$ bivalent aliphatic hydrocarbon group and may be joined to the aromatic ring system at the 2, 3, 8 or 9 positions. n is 0 to 3.

Of the compounds of formula (I) those of formula (II), wherein $R^1$ is as defined herein above, and $R^5$ is a single bond or —CH=CH—, are preferred.

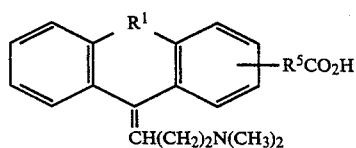

(II)

The most preferred compounds of formula (II), are those of formula (IIa) and formula (IIb) wherein $R^5$ is as defined for formula (II)

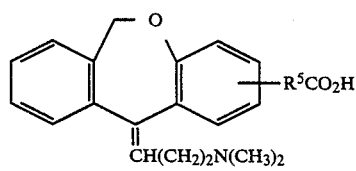

(IIA)

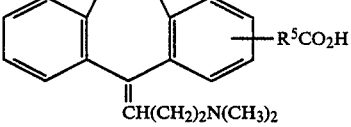

(IIB)

Examples of compounds of formula (IIA) include:
(1) (Z)-11-(3-(Dimethylamino)propylidene)-6,11-dihydrodibenz[b,e]oxepin-2-carboxylic acid,
(2) (E)-11-(3-(Dimethylamino)propylidene)-6,11-dihydrodibenz[b,e]oxepin-2-carboxylic acid,
(3) (E)-11-(3-(Dimethylamino)propylidene)-6,11-dihydrodibenz[b,e]oxepin-3-carboxylic acid,
(4) (Z)-11-(3-(Dimethylamino)propylidene)-6,11-dihydrodibenz[b,e]oxepin-3-carboxylic acid,
(5) (E)-11-(3-(Dimethylamino)propylidene)-6,11-dihydrodibenz[b,e]oxepin-8-carboxylic acid,
(6) (Z)-11-(3-(Dimethylamino)propylidene)-6,11-dihydrodibenz[b,e]oxepin-8-carboxylic acid,
(E)-11-(3-(Dimethylamino)propylidene)-6,11-dihydrodibenz[b,e]oxepin-9-carboxylic acid,
(8) (Z)-11-(3—(Dimethylamino)propylidene)-6,11-dihydrodibenz[b,e]oxepin-9-carboxylic acid,
(9) (E)-11-(3-(Dimethylamino)propylidene)-6,11-dihydrodibenz[b,e]oxepin-2-acrylic acid,
(10) (Z)-11-(3-(Dimethylamino)propylidene)-6,11-dihydrodibenz[b,e]oxepin-2-acrylic acid.

Examples of compounds of formula (11B) include;
(11) (E)-5-(3-(Dimethylamino)propylidene)-10,11-dihydro-5H-dibenzo[a,d]cyclohepten-3-carboxylic acid,
(12) (Z)-5-(3-(Dimethylamino)propylidene)-10,11-dihydro-5H-dibenzo[a,d]cyclohepten-3-carboxylic acid.

The compounds of the present invention exist in either the cis (Z) or trans (E) isomers (in relation to the bridge oxygen in the case of formula (IIA) and the acid side chain in the case of formula (IIB)). If the compounds of formula (I) or (II) contain a double bond in the acid bearing side chain, i.e. $R^4$ or $R^5$, there exists a second possibility of Z and E isomeric forms. All such geometric isomers and the isomeric mixture of these compounds are included within the scope of the present invention. Salts, amides and esters of the compounds of the formula (I) and (II) are included within the scope of the invention. While esters and amides of the compounds of the formulae (I) and (II) have antihistamine activity in their own right, they may also be useful intermediates in the preparation of the carboxy compounds of the formulae (I) and (II). Amides derived from ammonia, primary amines or amino acids, such as glycine, are particularly suitable. Suitable esters include conventional ester groups known to be useful for protecting carboxylic acid groups such as $C_{1-6}$ alkyl esters wherein the alkyl group is straight or branched chain and is optionally substituted by halogen. Alkyl esters ($C_{1-4}$) are particularly preferred.

Solvates of the compounds of the formulae (I) and (II) are also included within the scope of the present invention. Preferred solvates include hydrates and $C_{1-4}$ alkanolates.

Salts of the compounds of formula (I) may be either acid addition salts or salts formed with the carboxylic acid group. Acid addition salts are preferred but salts formed from the carboxylic acid group may be particularly useful in preparing the corresponding carboxy compound. When used in medicine, the salts of the compounds of formulae (I) and (II) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable acid addition salts include, but are not limited to, those prepared from the following acids: hydrochloric, sulphuric, nitric, phosphoric, maleic, salicylic, toluene-p-sulphonic, tartaric, citric, methanesulphonic, formic, malonic, isethionic, succinic, naphthalene—2—sulphonic and benzenesulphonic. Also, pharmaceutically acceptable salts can be prepared as ammonium salts, alkaline metal or alkaline earth salts, such as sodium, potassium or calcium salts of the carboxylic acid group.

The present invention also provides analogous methods for preparing compounds of formula (I), for example:

(a) (i) A compound of formula (I) may be prepared via the well known Wittig method (e.g., U.S. Pat. Nos. 3,354,155 and 3,509,175) by reaction of a compound of formula (III).

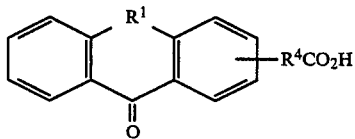

The Wittig reagent, $Ph_3P=CH(CH_2)_nNR_2R_3$; i.e., formula (IV), is conveniently

prepared by reacting a compound of the formula $Ph_3PCH_2(CH_2)_nNR_2R_3Br$, with a strong base, such as sodium hydride or $C_{1-6}$ alkyl lithium in a suitable inert solvent, such as tetrahydrofuran or dimethoxyethane at or near room temperature. It will be appreciated by those skilled in the art of organic chemistry that protection of the carboxy group may be desirable or required prior to the Wittig reaction and deprotection after the reaction.

(ii) A compound of formula (I) also may be prepared via the well known Grignard conditions (e.g., Belg. 623,259) in which a Grignard reagent, i.e. $(R^2R^3NCH_2CH_2CH_2Mg\ X$ where X is a halogen atom, reacted with a compound of formula (III), followed by dehydration with a strong acid.

(b) A compound of formula (I) wherein $R^4$ is a single bond can be prepared by carboxylation of a compound of formula (V)

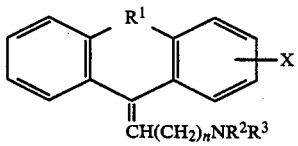

wherein $R^1$, $R^2$, $R^3$ and n are as defined, vide supra and X is a hydrogen or halogen atom (suitably a bromine or chloride atom attached directly to the ring system in the 2, 3, 8 or 9 positions. For example, a compound of formula (V) can be treated with a metalating agent such as butyl lithium followed by a reaction with carbon dioxide. When X is hydrogen separation of isomers may be required to obtain the desired compound of formula (I). When X is a halogen atom, a compound of formula (V) can be reacted with magnesium in an appropriate solvent followed by reaction with carbon dioxide via the Grignard procedure (The Merck Index, ninth ed., page ONR-38, Merck and Co., Rahway, N.J. (1976).

(c) A compound of formula (I) wherein $R^4$ is other than a single bond can be synthesized by reacting a compound of formula (V) (wherein X is a halogen atom) with a compound of formula (VI),

$$CH_2=CH-R^6-COR^7 \qquad (VI)$$

wherein $R^6$ is a $C_{1-5}$ bivalent aliphatic hydrocarbon and $R^7$ is a removable carboxylic acid protecting group such as one derived from a reaction of the carboxylic acid group which has been activated (e.g. converted to an acyl chloride) with an alcohol or amine. In some cases this reaction may need to be facilitated by a palladium catalyst (J. Org. Chem. 42, 3903–3907(1977)). A variation of this method involves a reaction of a compound of formula (VII) with a compound of formula IV in a similar manner, vide supra, followed by catalytic reduction of the double bond in the carboxylic bearing side chain that followed by the Wittig reaction described in Section (a) (i) or (ii), vide supra. The carboxylic acid groups may then be regenerated by deprotection if required.

(d) When the preparation of a compound of the formula (I) wherein $R^4$ is $CH=CH$ is required, a compound of the formula (VII)

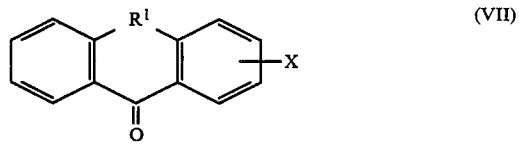

wherein $R^1$ is as defined, vide supra and X is halogen can be reacted with acrylic acid or an acrylic acid ester, with use of a catalyst if needed, by a method analogous to that described in (b), vide supra, followed by a Wittig reaction as described in part (a) (i) or (ii), vide supra. The carboxylic acid can be regenerated by deprotection if desired.

A compound of formula (VII) may be prepared by reacting a compound of formula (VIII).

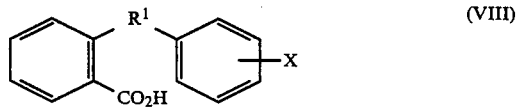

wherein $R^1$ and X are as defined, vide supra with a dehydrating agent such as $(CF_3CO)_2O/BF_3.OEt_2$.

(e) It is possible to convert one compound of the formula (III) to another compound of the formula (III) by methods well known to those skilled in the art, for example the reduction of one or more double bonds or de-esterification of an ester group or hydrolysis of an amide, followed by a Wittig reaction with $Ph_3P=CH_2(CH_2)_nNR_2R_3$ as described, vide supra.

(f) A compound of formula (VIII) can be converted to a Grignard reagent or an organolithium reagent by methods well know to those skilled in the art (after protecting the $CO_2H$ group) then reacted with dimethyl formamide to obtain the corresponding aldehyde. Such an aldehyde can be converted to an acid by oxidation or reaction with a trialkyl phosphonium acetate or an equivalent. By methods well known in the art of organic chemistry, after deprotecting such an acid can be dehydrated as described in (d), vide supra to give a compound of formula (III).

(g) A compound of the formula (V) where X is halogen can be reacted with a metal (I) cyanide, such as cuprous cyanide to give a corresponding carbonitrile derivative, which can then be converted to compounds of formula (I), eg the carboxylic acid via hydrolysis.

Those intermediates that are novel form an important further aspect of the present invention.

(h) Interconversion of compounds of the formula (I) is possible, e.g. by hydrolysis of esters, amides and by isomerization about the multiple bonds when such bonds are present or by selective reduction of multiple bonds when such bonds are present.

The compounds of this invention having antiallergic activity may be used for the same indications as clinically used antiasthmatic compounds, namely to help to control bronchoconstriction or brochospasm characteristic of allergic asthma and exercise induced asthma and the symptoms of bronchoconstriction and bronchospasm resulting from acute or chronic bronchitis. The compounds are believed to inhibit the release of autacoids (i.e. histamine, serotonin and the like) from mast cells and to inhibit directly the antigen-induced production of histamine. Thus, they may be classified as mast cell stabilizers with antihistaminic action.

The compounds of this invention having antihistamine activity may be used for the same indications as clinically used antihistamines, namely to relieve detrimental symptoms (caused by histamine release) of nasal stuffiness due to colds and vasomotor rhinitis and for the symptomatic control of allergic conditions including nasal allergy, perennial rhinitis, urticaria, angioneurotic oedema, allergic conjunctivitis, food allergy, drug and serum reactions, insect bites and stings and desensitizing reactions. The compound may also be used in conditions response to its antipruritic activity including allergic dermatoses, neurodermatitis, anogenital pruritus, and pruritus of non-specific origin such as eczema, and of specific cause such as chickenpox, photosensitivity and sunburn. The present invention therefore provides a method for the symptomatic treatment of allergic conditions by the administration of an effective amount of a compound of formula (I). The present invention also provides a method for the antagonism of endogenously released histamine by the administration of an effective amount of a compound of formula (I). The compounds of formula (I) are substantially free from sedative effects.

The amount of active compound, ie, a compound of formula (I) required for use in the above conditions will vary with the compound chosen, the route of administration and the condition and mammal undergoing treatment, and is ultimately at the discretion of the physician. A suitable oral dose of the active compound for a mammal is in the range of from 0.003 to 1.0 mg per kilogram body weight per day; preferably from 0.04 to 0.24 mg/kg. For example a typical dose for a human recipient of compound (1), (Z)-11—(3—(dimethylamino)propylidene)—6,11—dihydrodibenz[b,e]oxepin—2—carboxylic acid, as the hydrogen chloride salt (see Example 7 and Table 1, vide infra) is between 0.03 and 0.1 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.014 to 0.08 mg/kg body weight; for example, a typical sub-dose of such a compound for a human recipient is between 1 and 20 mg, for example 4 or 8 mg.

While it is possible for a compound of formula (I) to be administered alone as the raw chemical, it is preferable to present the compound of formula (I) as a pharmaceutical formulation. Thus, the present invention also provides pharmaceutical formulations, both for veterinary and for human medical use, which comprise a compound of formula (I) together with one or more pharmaceutically acceptable carriers therefor and optionally any other therapeutic ingredients. For example, the active compound may be formulated with a sympathomimetic agent such as the decongestant pseudoephedrine, an antitussive such as codeine, an analgesic, an antiinflammatory, an antipyretic, or an expectorant. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or nonaqueous liquid such as a syrup, and elixir, an emulsion or a draught. A tablet may be made by compression or molding, optionally with one or more accessory ingredients. Compressed tablets may be prepared by compressing in a suitable machine, with the active compound being in a free-flowing form such as a powder or granules which is optionally mixed with binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol, for example glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except that the pH and isotonic factors are adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

The present invention also provides the first use of the compounds of formula (I) in medicine.

The following Examples are provided by the way of illustration of the present invention and should in no way be construed as a limitation thereof. All temperatures indicated are in degrees Celsius.

EXAMPLE 1

(E)/(Z)-11-(3-(Dimethylamino)propylidene)-6,11-dihydrodibenz[b,e]oxepin-2-carboxylic acid (a) 2-Bromo-6,11-dihydrodibenz[b,e]oxepin-11-one 2-Bromo-6,11-dihydrodibenz[b,e]oxepin-11-one was prepared as described in U.S. Pat. No. 4,282,365, m.p. 132°–134° C. (Lit. m.p. 136°–139° C.). pmr (DMSO/$d_6$) δ: 8.13 (d, J=2.6 Hz, 1H, $H_1$), 7.48–7.83 (m, 5H, aromatic), 7.07 (d, J=8.8 Hz, 1H, $H_4$), 5.31 (s, 2H, $CH_2O$).

Analysis: Calcd. for $C_{14}H_9BrO_2$: C, 58.16; H, 3.14; Br, 27.64. Found: C, 58.20; H, 3.18; Br, 27.73.

(b) (E)/(Z)-3-(2-Bromo-6,11-dihydrodibenz[b,e]oxepin-11-ylidene)-N,N-dimethylpropylamine Anhydrous 3-(dimethylamino)propyltriphenylphosphonium bromide hydrobromide (39.4 g., 0.08 mole) was suspended in 450 mL of dry tetrahydrofuran and 100 mL of a solution of n-butyl lithium in hexane (1.6M) was added dropwise at 0° C. under a nitrogen atmosphere during a 30 minute period. After an additional 10 minutes, 2-bromo-6,11-dihydrodibenz[b,e]oxepin-11-one (16.8 g., 0.06 mole) in 150 mL dry tetrahydrofuran was added slowly to the deep red solution and the reaction mixture was then refluxed for 18 hours. The reaction mixture was poured onto ice-water, and the mixture was extracted with diethyl ether. The ether layer was concentrated under reduced pressure and the residue was suspended in water and then acidified with 6N hydrochloric acid. The acidic aqueous layer was washed with hexanes and then was concentrated to give a gummy residue. The residue was crystallized from ethyl acetate/methanol to provide 5.3 g. of pure Z-isomer as its hydrochloride salt, m.p. 201°–204° C. The mother liquor was chromatographed on a silica gel column (Waters Associates-Prep. 500) with ethyl acetate/methanol (8:2) to give an additional 2.55 g. of pure Z-isomer as the hydrochloride salt and 2.79 g. of E-isomer as its hydrochloride salt, m.p. 230°–233° C. pmr (Z-isomer) (DMSO/$d_6$) δ: 7.25–7.44 (m, 6H, aromatic), 6.81 (degenerate d, J=9.1 Hz, 1H, $H_4$), 5.72 (t, J=7.1 Hz, 1H, CH=), 5.22 (s, 2H, $CH_2O$), 3.18 (m, 2H, $NCH_2$), 2.70 (m, 2H, $CH_2$), 2.66 (s, 6H, $NMe_2$). pmr (E-isomer) (DMSO/$d_6$) δ: 7.23–7.50 (m, 6H, aromatic), 6.70 (d, J=8.6 Hz, 1H, $H_4$), 6.10 (t, J=7.2 Hz, 1H, CH=) 5.15 (br s, 2H, $CH_2O$), 3.07 (m, 2H, $NCH_2$), 2.65 (s, 6H, $NMe_2$), 2.50 (m overlap with DMSO, 2H, $CH_2$).

(c) (Z)-11-(3-(Dimethylamino)propylidene)-6,11-dihydrodibenz[b,e]oxepin-2-carboxylic acid (Compound 1)

A solution of n-butyl lithium in hexane (1.6M, 3.5 mL) was added dropwise to a solution of 1.8 g. pure (Z)-3-(2-bromo-6,11-dihydrodibenz[b,e]oxepin-11-ylidene)-N,N-dimethylpropylamine in 100 mL of dry tetrahydrofuran at −70° C. under a nitrogen atmosphere. After the yellowish-orange solution was stirred at −70° C. for 10 minutes, gaseous carbon dioxide was bubbled through the reaction medium to give a pale yellow solution. The solution was allowed to warm gradually to room temperature and was then concentrated under reduced pressure. The foamy residue was dissolved in water, and the mixture was neutralized with 1N hydrochloric acid and then extracted with chloroform. Concentration of the chloroform and recyrstallization of the residue from water gave 0.5 g. pure Z-2-carboxylic acid, m.p. 121°–123° C. pmr (CDCl$_3$) δ: 7.87 (d, J≦1 Hz, 1H, $H_1$), 7.81 (dd, J=7.8, 2.2 Hz, 1H, $H_3$), 7.25–7.28 (m, 4H, aromatic), 6.82 (degenerate d, J=8.8 Hz, 1H, $H_4$), 6.45 (br s, 1H, $CO_2H$), 5.50 (m, 1H, CH=), 5.20 (br s, 2H, $CH_2O$), 2.92 (m, 4H, $NCH_2CH_2$), 2.66 (s, 6H, $NMe_2$).

Analysis: Calcd. for $C_{20}H_{21}NO_3 \cdot 0.55 H_2O$: C, 72.07; H, 6.68; N, 4.20. Found: C, 72.07; H, 6.69; N, 4.18.

(d) (E)-11-(3-(Dimethylamino)propylidine)-6,11-dihydrodibenz[b,e]oxepin-2-carboxylic acid (Compound 2)

Pure (E)-3-(2-bromo-6,11-dihydrodibenz[b,e]oxepin-11-ylidene)-N,N-dimethylpropylamine (1.55 g., .43 mmole), was treated under nitrogen in cold (−70° C.) tetrahydrofuran (100 mL) with 4.4 mmole of n-butyl lithium in hexane followed by gaseous carbon dioxide as described for the Z-isomer (Step C). Isolation of the (E)-2-carboxylic acid was achieved by through chromatography of the crude product on a reverse phase C18 semipreparative column eluted with 20% methanol in water (containing 0.1% triethylamine). Recrystallization of the solid product from water afforded 0.012 g of pure E-2-carboxylic acid, m.p. >200° C. (decomp.). pmr (CDCl$_3$) δ: 7.85 (d, J=2.0 Hz, 1H, $H_1$), 7.06–7.78 (m, 5H, aromatic), 6.47 (d, J=8.5 Hz, 1H, $H_4$), 6.28 (t, J=4.2 Hz, 1H, CH=), 5.85 (m, 1H, ArCH), 4.70 (m, 1H, ArCH), 2.43 (m, 4H, $NCH_2CH_2$), 2.28 (s, 6H, $NMe_2$).

Analysis: Calcd. for $C_{20}H_{21}NO_3 \cdot 0.50 H_2O$: C, 72.27; H, 6.67; N, 4.21. Found: C, 72.15; H, 6.46; N, 4.22.

EXAMPLE 2

(E)/(Z)-11-(3-(Dimethylamino)propylidene)-6,11-dihydrodibenz[b,e]oxepin-3-carboxylic acid Methyl 2-(3-bromophenoxymethyl)benzoate To a mixture of 3-bromophenol (60 g, 0.35 mole) and potassium carbonate (25 g, 0.18 mole) in 250 mL of N,N-dimethylformamide was added methyl α-bromo-2-toluate (65 g, 0.28 mole). The reaction mixture was stirred at room temperature for 18 hours, then heated on a steam bath for 3 hours. The mixture was poured into ice-water, and the solids were collected by filtration and washed with water to give the crude product. Analytical sample was obtained by recrystallization from methylene chloride/hexanes, m.p. 84°–85° c. pmr (CDCl$_3$) δ: 8.0 (m, 1H, H$_6$), 6.93–7.69 (m, 7H, aromatic H), 5.47 (s, 2H, ArCH$_2$O), 3.89 (s, 3H, CO$_2$CH$_3$).

Analysis: Calcd. for C$_{15}$H$_{13}$BrO$_3$: C, 56.09; H, 4.08; Br, 24.88. Found: C, 56.20; H, 4.12; Br, 24.77.

(b) 2-(3-bromophenoxy)methylbenzoic acid

Methyl 2-(3-bromophenoxy)methylbenzoate (34 g) was refluxed in a mixture of 100 mL of 10% sodium hydroxide and 200 mL of methanol for 3 hours. The reaction mixture was concentrate under reduced pressure and water was added to the residue. The mixture was then acidified with concentrated hydrochloric acid. Extracting the acidic solution with ethyl acetate and then concentration of the organic layer gave the 2-(3-bromophenoxy)methyl benzoic acid (35 g) m.p. 158°–159° C. pmr (CDCL$_3$) δ: 8.10 (m, 1H, H$_6$), 6.84–7.74 (m, 7H, aromatic H), 6.16 (br s, 1H, CO$_2$H), 5.49 (s, 2H, ArCH$_2$O).

Analysis: Calcd. for C$_{14}$H$_{11}$BrO$_3$: C, 54.74; H, 3.61; Br, 26.02. Found: C, 54.65; H, 3.61; Br, 26.08.

(c) 3-Bromo-6,11-dihydrodibenz[b,e]oxepin-11-one

A suspension of 2-(3-bromophenoxymethyl)benzoate (35 g, 0.11 mole) in 100 mL of trifluoroacetic anhydride containing 20 drops of boron trifluoride-ether complex was refluxed for 4 hours. The mixture was poured into ice-water and then extracted with diethyl ether. Concentration of ether solution under reduced pressure and chromatography of the residue on a silica gel column (Waters Associates, Prep 500) with hexane/methylene chloride (70:30) gave the pure product (14 g). m.p. 110°–112° C. pmr (CDCL$_3$) δ: 8.10 (d, J=9.1 Hz, 1H, H$_1$), 7.90 (dd, J=1.4, 7.6 Hz, 1H, H$_{10}$) 7.57 (dt, J=1.4, 7.4, 7.4 Hz, 1H H8), 7.48 (dt, J=1.4, 7.6, 7.6 Hz, 1H, H9), 7.36 (dd, J=1.3, 7.3 Hz, 1H, H$_7$), 7.27 (d, J=1.8 Hz, 1H, H$_4$), 7.24 (dd, J=1.8, 9.1 Hz, 1H, H$_2$), 5.18 (s, 2H, ArCH$_2$O).

Analysis: Calcd. for C$_{14}$H$_9$BrO$_2$: C, 58.16; H, 3.14; Br, 27.64. Found: C, 58.13; H, 3.19; Br, 27.72.

(d) (E)/(Z)-3-(3-Bromo-6,11-dihydrodibenz[b,e]oxepin-11-ylidene)-N,N-dimethylpropylamine Anhydrous 3-(dimethylamino)propyltriphenylphosphonium bromide hydrobromide (24.5 g, 48.0 mmole), 96 mmole of n-butyl lithium in hexane, and 3-bromo-6,11-dihydrodibenz[b,e]oxepin-11-one (10 g, 34.6 mmole) were reacted in 580 mL dry tetrahydrofuran by the procedure of Example I, step b. This provided an (E)/(Z)-(1:3) isomeric mixture of bromoamines (6.0 g). Recrystallization of half of the mixtures (3.0 g) from ethyl acetate gave 1.45 g of Z-isomer of ≧93% stereoisomeric purity (assayed by 'H-NMR) as a white solid. pmr (CDCl$_3$) δ: 7.23–7.31 (m, 4H, aromatic H), 6.92–7.05 (m, 3H, aromatic H), 5.91 (t, 1H, CH=, 7% E-isomer), 5.60 (t, 1H, CH=, 93% Z-isomer) 5.15 (very br s, 2H, ArCH$_2$O), 3.12 (m, 2H, CH$_2$), 2.99 (m, 2H, NCH$_2$), 2.78 (s, 6H, NMe$_2$, 93% Z-isomer), 2.71 (s, 6H, NMe$_2$, 3% E-isomer).

Analysis: Calcd. for C$_{19}$H$_{20}$BrNO.1.0 HCl: C, 57.81; H, 5.36; N, 3.55. Found: C, 57.62; H, 5.33; N, 3.54.

(e) (E)/(Z)-11-(3-(Dimethylamino)propylidene)-6,11-dihydrodibenz[b,e]oxepin-3-carboxylic acid (Compounds 3/4)

An isomeric mixture E/Z (1:3) of 3-(3-bromo-6,11-dihydrodibenz[b,e]-11-ylidene]-N,N-dimethylpropylamine (3.0 g, 8.5 mmole) in 150 mL dry tetrahydrofuran at −70° C. was reacted with 9.4 mmole n-butyl lithium in hexane followed by gaseous carbon dioxide by the procedure of Example 1, step c, to provide the corresponding carboxylic acids as an E/Z (1:3) stereoisomeric mixture. The mixture was chromatographed on a reverse phase PRP-1 semi-preparative column with water/acetonitrile (87:13) to provide 0.08 g of E-isomer (lyophilized powder) and 0.50 g of Z-isomer (lyophilized powder). pmr (E-isomer) (CDCl$_3$/TFA) δ: 7.85 (dd, J=8.0, 1.7 Hz, 1H, H$_2$) 7.50 (d, J=1.7 Hz, 1H, H$_4$), 7.32–7.43 (m, 4H, aromatic H), 7.16 (m, 1H, H$_1$), 5.99 (t, 1H, CH=), 5.50 (br s, 1H, ArCHO), 4.85 (br s, 1H, ArCHO), 3.25 (q, 2H, CH$_2$), 2,86 (s, 3H, NMe), 2.85 (s, 3H, NMe), 2.70 (q, 2H, NCH$_2$). pmr (Z-isomer) (CDCL$_3$/TFA) δ: 7.26 (m, 2H, H$_2$ and H$_4$), 7.24–7.36 (m, 4H, aromatic H), 7.16 (m, 1H, H$_1$), 5.71 (t, 1H, CH=), 5.20 (very br s, 2H, ArCH$_2$O), 3.32 (q, 2H, CH$_2$), 2.91 (s, 3H, NMe), 2.90 (s, 3H, NMe), 2.89 (m, 2H, NCH$_2$).

Analysis: Calcd. for C$_{20}$H$_{21}$NO$_3$.0.5 HCl.0.2 H$_2$O: C, 69.58; H, 6.39; N, 4.06. Found (E-isomer): C, 69.64; H, 6.25; N, 4.03. Calcd. for C$_{20}$H$_{21}$NO$_3$.0.25 H$_2$O: C, 73.26; H, 6.61; N, 4.27. Found (Z-isomer): C, 73.20; H, 6.60; N, 4.20.

EXAMPLE 3

(E)/(Z)-(11-(3-Dimethylamino)propylidene)-6,11-dihydrodibenz[b,e]oxepin-8-carboxylic acid (a) 8-Bromo-6,11-dihydrodibenz[b,e]oxepin-11-one Phenol (8 g, 85 mmole) and potassium carbonate (11.7 g, 85 mmole) in 150 mL of N,N-dimethylformamide was reacted with methyl 4-bromo-α-bromo-2-toluate (20 g, 65 mmole) by the procedure of Example 2, step a and folloed with alkaline hydrolysis by the procedure of Example 2, step b to give the crude 4-bromo-2-phenoxybenzoic acid (13 g) which was used without further purification.

The crude 4-bromo-(2-phenoxymethyl)benzoic acid (13 g, 42 mmole) was cyclized in 50 mL of trifluoroacetic anhydride containing 1 mL of boron trifluorideether complex by the procedure of Example 2, step c. The solid was collected by filtration and washed with water to give 11.9 g of the tricyclic ketone, m.p. 125°–126° C. pmr (CDCL$_3$) δ: 8.17;14 8.30 (m, 1H, H1), 6.99–7.86 (m, 6H, aromatic H), 5.14 (s, 2H, ArCH$_2$O).

Analysis: Calcd. for C$_{14}$H$_9$BrO$_2$: C, 58.16; H, 3.14; Br, 27.64. Found: C, 58.15; H, 3.17; Br, 27.73.

(b)
(E)/(Z)-3-(8-Bromo-6,11-dihydrodibenz[b,e]oxepin-11-ylidene)-N,N-dimethylpropylamine Anhydrous 3-(dimethylamino)propyltriphenylphosphonium bromide hydrobromide (24.5 g, 48 mmole), 96 mmole of n-butyl lithium in hexane, and 8-bromo-6,11-dihydrodibenz[b,e]oxepin-11-one (10 g, 34.6 mmole) were reacted in 580 mL dry tetrahydrofuran by the procedure of Example I, step b. This provided an E/Z (1:3.5) isomeric mixture of bromoamines. Recrystallization of the mixture from diethyl ether gave 0.17 g of Z-isomer and 1.8 g of an E/Z (1:4) (assayed by HPLC on C18) isomeric mixture which was used in the next step without further purification. pmr (Z-isomer) (CDCl$_3$) δ: 7.38–7.44 (m, 2H, H$_7$ and H$_9$); 7.13–7.18 (m, 3H, aromaatic H); 6.84–6.93 (m, 2H, H$_2$ and H$_4$); 5.70 (t, 1H, CH=); 5.15 (br s, 2H, ArCH$_2$O); 2.55 (q, 2H, CH$_2$); 2.43 (t, 2H, NCH$_2$); 2.22 (s, 6H, NMe$_2$).

Analysis: Calcd. for C$_{19}$H$_{20}$BrNO: C, 63.70; H, 5.63; N, 3.91. Found (Z-isomer): C, 63.85; H, 5.65; N, 3.92.

(c)
(E)/(Z)-11-(3-(Dimethylamino)propylidene)-6,11-dihydrodibenz[b,e]oxepin-8-carboxylic acid (Compounds 5/6)

An isomeric mixture E/Z (1:4) of 3-(8-bromo-6,11-dihydrodibenz[b,e]-11-ylidene)-N,N-dimethylpropylamine (1.8 g, 5.0 mmole) in 100 mL dry tetrahydrofuran at −70° C. was reacted with 5.5 mmole n-butyl lithium in hexane followed by gaseous carbon dioxide by the procedure of Example I, step c, to provide the corresponding carboxylic acid as an E/Z (1:5) stereoisomeric mixture. The mixture was chromatographed on a reverse phase PRP-1 semi-preparative column with water/acetonitrile (85:15) to provide 0.05 of E-isomers (lyophilized powder) and 0.28 g of Z-isomer (lyophilized powder). pmr (E-isomer) (CDCl$_3$) δ: 7.94 (br s, 1H, H$_9$), 7.70 (br s, 1H, CO$_2$H), 7.20–7.30 (m, 4H aromatic H), 7.14 (m, 1H, H$_3$), 6.87 (m, 1H, H$_2$), 6.76 (m, 1H, H$_4$), 5.88 (t, 1H, CH=), 5.54 (br s, 1H, ArCHO), 4.85 (br s, 1H, ArCHO), 3.00 (m, 2H, CH$_2$), 2.78 (m, 2H, NCH$_2$), 2.60 (s, 6H, NMe$_2$) pmr (Z-isomer) (CDCl$_3$) δ: 7.55 (d, J=7.0 Hz, 1H, H$_9$), 7.30 (br s, 1H, CO$_2$H), 7.00–7.25 (m, 4H, aromatic H), 6.84 (m, 2H H$_2$ and H$_4$), 5.95 (t, 1H, CH=), 5.70 (br s, 1H, ArCHO), 4.80 (br s, H, ArCHO), 3.35 (br s, 1H, CHC=), 2.50–3.00 (m, 3H, CHC= and NCH$_2$), 2.46 (s, 6H, NMe$_2$)

Analysis: Calcd. for C$_{20}$H$_{21}$NO$_3$.HCl.0.4 H$_2$O: C, 65.44; H, 6.26; N, 3.82. Found (E-isomer): C, 65.55; H, 6.51; N, 3.91. Calcd. for C$_{20}$H$_{21}$NO$_3$.2.2 H$_2$O: C, 66.17; H, 7.05; N, 3.86. Found (Z-isomer): C, 66.25; H, 6.93; N, 3.83.

EXAMPLE 4
(E)/(Z)-11-(3-(Dimethylamino)propylidene)-6,11-dihydrodibenz[b,e]oxepin-9-carboxylic acid (a) 9-Bromo-6,11-dihydrodibenz[b,e]oxepin-11-one 9-Bromo-6,11-dihydrodibenz[b,e]oxepin-11-one was prepared as described in U.S. Pat. No. 4,282,365, m.p. 104°–106° C. (Lit. m.p. 107.5°–108.5° C.). pmr (CDCl$_3$) δ: 8.02–8.27 (m, 2H, H$_1$ and H$_{10}$), 6.98–7.73 (m, 5H, aromatic), 5.14 (s, 2H, CH$_2$O).

Analysis: Calcd. for C$_{14}$H$_9$BrO$_2$: C, 58.16; H, 3.14; Br, 27.64. Found: C, 58.24; H, 3.18; Br, 27.51.

(b)
(E)/(Z)-3-(9-Bromo-6,11-dihydrodibenz[b,e]oxepin-11-ylidene)-N,N-dimethylpropylamine.

Anhydrous 3-(dimethylamino)propyltriphenylphosphonium bromide hydrobromide (31 g., 60.9 mmole), 122 mmole of n-butyl lithium in hexane, and 9-bromo-6,11-dihydrodibenz[b,e]oxepin-11-one (12.7 g., 43.8 mmole) were reacted in 750 mL dry tetrahydrofuran by the procedure of Example I, Step b. This provided an E/Z (1:6) isomeric mixture of bromoamines. Recrystallization of the mixture from ethyl acetate/methanol gave 1.2 g. of pure Z-isomer as its hydrochloride salt, melting range 91°–100° C. and 2.16 g. of an E/Z (1:4) isomeric mixture which was used in the next step without further purification. pmr (Z-isomer) (CDCl$_3$) δ: 6.94–7.46 (m, 7H, aromatic), 5.64 (t, J=8.0 Hz, 1H, CH=), 5.15 (br s, 2H, CH$_2$O), 3.07 (m, 4H, NCH$_2$CH$_2$), 2.75 (s, 6H, NMe$_2$).

Analysis: Calcd. for C$_{19}$H$_{20}$BrNO.HCl: C, 57.80; H, 5.36; N, 3.54. Found (Z-isomer): C, 57.56; H, 5.41; N, 3.45.

(c)
(E)-11-(3-(Dimethylamino)propylidene)-6,11-dihydrodibenz[b,e]oxepin-9-carboxylic acid (Compound 7)

An isomeric mixture E/Z (1:4) of 3-(9-bromo-6,11-dihydrodibenz[b,e]-11-ylidene)-N,N-dimethylpropylamine (2.0 g., 5.6 mmole) in 100 mL dry tetrahydrofuran at −70° C. was reacted with 6.2 mmole n-butyl lithium in hexane followed by gaseous carbon dioxide by the procedure of Example I, Step c, to provide the corresponding carboxylic acids as an E/Z (1:4) stereoisomeric mixture. The mixture was chromatographed on a reverse phase PRP-1 semi-preparative column with water/acetonitrile (85:15) to provide 0.06 g of E-isomer of ≧95% stereoisomeric purity (assayed by HPLC on C18) as pale yellow glass. pmr (DMSO-d$_6$) δ: 7.83 (d, J≦1 Hz, 1H, H$_{10}$), 7.79 (dd, J=7.2, 1.5 Hz, 1H, H$_8$), 6.69–7.39 (m, 5H, aromatic), 5.85 (t, J=6.4 Hz, 1H, CH=), 5.22 (s, 2H, CH$_2$O), 2.81 (m, 4H, NCH$_2$CH$_2$), 2.61 (s, 6H, NMe$_2$).

Analysis: Calcd. for C$_{20}$H$_{21}$NO$_3$.2.8H$_2$O: C, 64.26; H, 7.17; N, 3.75. Found: C, 64.23; H, 6.84; N, 3.76.

(d)
(Z)-11-(3-(Dimethylamino)propylidene)-6,11-dihydrodibenz[b,e]oxepin-9-carboxylic acid (Compound 8)

Pure (Z)-3-(9-bromo-6,11-dihydrodibenz[b,e]oxepin-11-ylidene)-N,N-dimethylpropylamine (0.78 g., 2.2 mmole), in cold (−70° C.) dry tetrahydrofuran (50 mL), was treated with 2.4 mmole n-butyl lithium in hexane followed by gaseous carbon dioxide by the procedure of Example I, Step c. This provided the desired carboxylic acid which was recrystallized from water to yield 0.15 g. pure Z-isomer, m.p. >205° C. (decomp.) with melting at 210° C. pmr (CDCl$_3$/D$_2$O) δ: 7.84 (d, J=1.8 Hz, 1H, H$_{10}$), 7.81 (dd, J=6.4, 1.8 Hz, 1H, Hg), 6.94–7.35 (m, 5H, aromatic), 5.78 (t, J=6.9 Hz, 1H, CH=), 5.25 (s, 2H, CH$_2$O), 3.20 (m, 2H, NCH$_2$), 2.80 (s, 6H, NMe$_2$), 2.50–2.90 (m, 2H, CH$_2$).

Analysis: Calcd. for C$_{20}$H$_{21}$NO$_3$.0.33H$_2$O: C, 73.06; H, 6.62; N, 4.26. Found: C, 72.92; H, 6.59; N, 4.13.

EXAMPLE 5

(E)/(Z)-11-(3-(Dimethylamino)propylidene)-6,11-dihydrodibenz[b,e]oxepin-2-(E)-acrylic acid

(a) Ethyl (E)-6,11-dihydro-11-oxodibenz[b,e]oxepin-acrylate

A mixture of palladium acetate (0.4 g, 1.73 mmole), triphenylphosphine (0.9 g, 3.46 mmole), 2-bromo-6,11-dihydro-11-oxodibenz[b,e]oxepin (10 g, 34.6 mmole), ethyl acrylate (13 g, 130 mmole) and tri-n-butylamine (7.7 g, 57 mmole) was heated at 130°–140° C. under a nitrogen atmosphere for six hours. The reaction mixture was partitioned between diethyl ether (100 mL) and 0.1N hydrochloric acid (50 mL). Evaporation of the ether under reduced pressure gave a yellow solid residue. The crude material was chromatographed on a silica gel column (Waters Associates-Prep 500) with hexanes/ethyl acetate (8:2) to give 6.12 g of (E)-acrylate product. Recrystallization from ethyl acetate/hexanes gave an analytical sample, m.p. 113°–114° C. pmr (CDCl$_3$) δ: 8.39 (d, J=2.4 Hz, 1H, H$_1$), 7.88 (dd, J=1.5, 7.5 Hz, 1H, H$_{10}$), 7.70 (d, J=16.4 Hz, 1H, ArCH=), 7.66 (dd, J=2.2, 8.6 H$_z$, 1H, H$_3$), 7.46–7.60 (m, 2H, H$_8$ and H$_9$), 7.38 (dd, J=1.0, 7.3 Hz, 1H, H$_7$), 7.07 (d, J=8.6 H$_z$, 1H, H$_4$), 6.42 (d, J=16.0 Hz, 1H, =CHCO$_2$), 5.23 (s, 2H, ArCH$_2$O), 4.26 (q, 2H, CH$_2$), 1.34 (t, 3H, CH$_3$).

Analysis: Calcd. for C$_{19}$H$_{16}$O$_4$: C, 74.01; H, 5.23. Found: C, 73.90; H, 5.28.

(b) (E)/(Z)-11-(3-(Dimethylamino)propylidene)-6,11-dihydrodibenz[b,e]oxepin-2(E)-acrylic acid (Compounds 9/10)

Anhydrous 3-(dimethylamino)propyltriphenylphosphonium bromide hydrobromide (0.8 g, 1.57 mmole) was suspended in 20 mL of dry tetrahydrofuran and 1.8 mL of a solution of n-butyl lithium in hexane (1.6M) was added dropwise at 0° C. under a nitrogen atmosphere during a 10 minute period. After an additional 10 minutes, ethyl (E)-6,11-dihydro-11-oxodibenz[b,e]oxepin-2-acrylate (0.34 g, 1.1 mmole) in 5 mL dry tetrahydrofuran was added slowly to the deep red solution and the reaction mixture was then refluxed for 18 hours. The reaction was worked up as described in Example I, step d. The crude material was dissolved in 1N sodium hydroxide (20 mL) and 20 mL of absolute ethanol, and then stirred at room temperature for 18 hours. After neutralization with 1N hydrochloric acid (20 mL) the solution was evaporated to dryness and the residue was chromatographed on a PRP-1 column with water-/acetonitrile (78:22) to give 0.015 g of Z-isomer (lyophilized solid) and 0.009 g of E-isomer (lyophilized powder). pmr (Z-isomer) (CD$_3$OD) δ: 7.29–7.38 (m, 7H, aromatic H and ArCH=), 6.82 (d, J=8.5 Hz, 1H, H$_4$) 6.37 (d, J=16.0 H$_z$, 1H, =CHCO$_2$), 5.70 (t, 1H CH=), 5.20 (very br s, 2H, ArCH$_2$O), 2.87 (m, 2H, CH$_2$), 2.77 (m, 2H, NCH$_2$), 2.50 (s, 6H, NMe$_2$). pmr (E-isomer) (CD$_3$OD) δ: 7.28–7.49 (m, 7H, aromatic H and ArCH=), 6.72 (d, J=8.5 H$_z$, 1H, H$_4$), 6.35 (d, J=16.0 H$_z$, 1H, =CHCO$_2$), 6.10 (t, 1H, CH=), 5.58 (very br s, 2H, ArCH$_2$O), 2.78 (m, 2H, CH$_2$), 2.50 (m, 2H, NCH$_2$), 2.40 (s, 6H, NMe$_2$).

EXAMPLE 6

(E)/(Z)-5-(3-(Dimethylamino)propylidine)-10,11-dihydro-5H-dibenzo[a,d]cyclohepten-3-carboxylic acid

(a) (E)/(Z)-3-(3-Bromo-10,11-dihydrodibenzo[a,d]cyclohepten-5-ylidene)-N,N-dimethylpropylamine Anhydrous 3-(dimethylamino)propyltriphenylphosphonium bromide hydrobromide (21 g., 40.8 mmole) was suspended in 400 ml. of dry tetrahydrofuran and n-butyl lithium in hexane (82 mmole) was added dropwise at 0° C. under a nitrogen atmosphere during a period of 0.5 hour. After an additional 10 minutes, 9.0 g. (31.3 mmole) of 3-bromo-10,11-dihydro-5H-dibenzo[a,d]cyclohepten-5-one, prepared as described in C. A. Stone, J. M. Stavorski, H. C. Wenger and C. T. Ludden, J. Med. Chem. (1965) 8, 829, in 100 ml. dry tetrahydrofuran was added slowly to the deep red solution and the reaction was then refluxed for 18 hours. The solution was poured into ice-water and the mixture was extracted with diethyl ether. Evaporation of the ether under reduced pressure gave an oily residue which was suspended in water and the mixture was then acidified with 6N hydrochloric acid. The acidic aqueous solution was washed with hexanes, and then concentrated under reduced pressure. The residue was chromatographed on a silica gel Prep 500 column with methanol to provide an E/Z (1:1) stereoisomeric mixture of bromoamines. Recrystallization of the isomeric mixture from methanol gave 0.5 g. of the pure E-isomer as its hydrochloric salt, m.p. 239°–240° C. The residue from the mother liquor was chromatographed on a reverse phase C18 semi-preparative column with 70% methanol in water (containing 0.1% triethylamine). The appropriate fractions were pooled and recrystallized from methanol/water to yield 1.13 g. of the Z-isomer (with the presence of 5% E-isomer) as the free base, m.p. 73°–75° C. Also, the fractions containing the E-isomer were pooled, evaporated and recrystallized from methanol/ethyl acetate to give 0.70 g. of the E-isomer as the free base. From other fractions 3.5 g. of E/Z (1:1) isomeric mixture was collected which could be used either for further separation or for carboxylation in the next step. pmr (E-isomer, free base) (CDCl$_3$) δ: 7.43 (d, J=1.9 Hz, 1H, H$_4$), 7.12–7.26 (m, 5H, aromatic), 6.89 (d, J=8.3 Hz, 1H, H$_1$), 5.88 (t, J=7.3 Hz, 1H, CH=), 3.30 (m, 2H, CH$_2$Ar), 2.84 (m, 2H, CH$_2$Ar), 2.28–2.38 (m, 4H, NCH$_2$CH$_2$), 2.16 (s, 6H, NMe$_2$). pmr (≧95% stereoisomeric pure Z-isomer, free base) (CDCl$_3$) δ: 7.00–7.33 (m, 7H, aromatic), 5.86 (t, J=7.3 Hz, 1H, CH=), 3.30 (m, 2H, CH$_2$Ar), 2.90 (m, 1H, CHAr), 2.70 (m, 1H, CHAr), 2.26–2.37 (m, 4H, NCH$_2$CH$_2$), 2.18 (s, 6H, NMe$_2$).

Analysis: Calcd. for C$_{20}$H$_{22}$BrN.HCl: C, 61.16; H, 5.90; N, 3.57. Found: (E-isomer): C, 61.24; H, 5.89; N, 3.51. Calcd. for C$_{20}$H$_{22}$BrN: C, 67.42; H, 6.22; N, 3.93. Found: (≧95% stereoisomeric pure Z-isomer): C, 67.72; H, 6.42; N, 3.86.

(b) (E)/(Z)-5-(3-(Dimethylamino)propylidene)-10,11-dihydro-5H-dibenzo[a,d]cyclohepten-3-carboxylic acid (Compounds 11/12)

A solution of n-butyl lithium (6 mmole) was added dropwise to an E/Z (1:1) isomeric mixture of 3-(3-bromo-10,11-dihydrodibenzo[a,d]cyclohepten-5-ylidene)-N,N-dimethylpropylamine (1.98 g., 5.6 mmole)

in 100 ml. dry tetrahydrofuran at −70° C. under a nitrogen atmosphere. After the yellowish orange solution was stirred at −70° C. for an additional 10 minutes, gaseous carbon dioxide was bubbled through the reaction medium for 30 min. to give a pale yellow solution. The reaction mixture was allowed to warm gradually to room temperature, and was then concentrated under reduced pressure. The residue was dissolved in water, and then the solution was neutralized with 1N hydrochloric acid. The crude E/Z (1:1) mixture was chromatographed on a reverse phase PRP-1 semi-preparative column with 15% acetonitrile in water to give 0.05 g. of the E-isomer and 0.08 g. of the Z-isomer. Both isomers were obtained as lyophilized powders, without definitive melting points. Rechromatography of the resulting isomeric mixture (0.8 g.) yielded more pure E-isomer (0.09 g.), Z-isomer (0.16 g.) and also an E/Z (1:1) isomeric mixture (0.10 g). pmr (E-isomer) (DMSO/$d_6$) δ: 7.79 (d, J=1.6 Hz, 1H, $H_4$), 7.68 (dd, J=7.9, 1.6 Hz, 1H, $H_2$), 7.12–7.29 (m, 5H, aromatic), 5.88 (t, J=7.2 Hz, 1H, CH=), 3.30 (m, 2H, $CH_2Ar$), 2.85 (m, 2H, $CH_2Ar$), 2.35–2.45 (m, 4H, $NCH_2CH_2$), 2.10 (s, 6H, $NMe_2$). pmr (Z-isomer) (DMSO/$d_6$) δ: 7.78 (dd, J=7.8, 1.7 Hz, 1H, $H_2$), 7.66 (d, J=1.5 Hz, 1H, $H_4$), 7.36 (d, J=7.8 Hz, 1H, $H_1$), 7.04–7.26 (m, 4H, aromatic), 5.86 (t, J=7.2 Hz, 1H, CH=), 3.32 (m, 2H, $CH_2Ar$), 2.85, (m, 2H, $CH_2Ar$), 2.10–2.44 (m, 4H, $NCH_2CH_2$), 2.07 (s, 6H, $NMe_2$).

Analysis: Calcd. for $C_{21}H_{23}NO_2 \cdot 2.2H_2O$: C, 69.86; H, 7.65; N, 3.88. Found: (E-isomer): C, 69.66; H, 7.34; N, 3.92. Found (Z-isomer): C, 69.69; H, 7.37; N, 3.95.

EXAMPLE 7

Antihistamine Activity

A. In vitro antihistamine activity

The longitudinal muscle was isolated from the intact ileum of guinea-pigs (Hartley, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration response curve was run. Shifts to the right of the agonist concentration-response curve produced by the antagonists were used to construct Schild plots (Arunlakshana, O. and Schild, H. O., *Br. J. Pharmacol.* 14, 48–58, 1959). Regression of Log (dr-1) on Log [B], where dr is an equiactive response in the presence and absence of antagonist and [B] is the molar concentration of antagonist, allowed an estimate of $pA_2$, i.e. the negative log of the concentration of antagonist which shifts the control histamine concentration response curve 2× to the right.

TABLE I

Antihistaminic Activity in In Vitro Assays

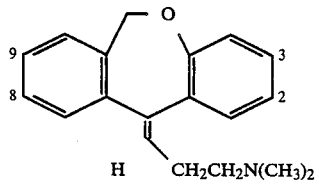

| Compound No. | Compound | $pA_2$ |
| --- | --- | --- |
| — | Doxepin[a] | 9.7 |

TABLE I-continued

Antihistaminic Activity in In Vitro Assays

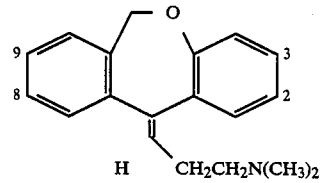

| Compound No. | Compound | $pA_2$ |
| --- | --- | --- |
| 1 | Z-2-$CO_2H$ | 8.3 |
| 2 | E-2-$CO_2H$ | 8.3 |
| 6 | Z-8-$CO_2H$ | 6.7 |
| 7 | E-9-$CO_2H$ | 9.2 |
| 8 | Z-9-$CO_2H$ | 7.8 |

[a]The Doxepin sample tested here had a Z:E ratio of 4:1

B. In vivo Antihistaminic Activity

Guinea pigs (Hartley, male, 300–350 g) were fasted for 20 hours and then dosed p.o. or i.p. with the test compound. One hour after dosing, on an individual basis, the guinea pigs were placed in a clear plastic chamber which was saturated and continually gassed with 0.25% histamine from an aerosol nebulizer. The guinea pigs were monitored for signs of histamine anaphylaxis (e.g. cough, sneeze, strong abdominal movements, cyanoses or loss of righting). Under the test conditions, control animals collapsed on average within 33 seconds. $ED_{50}$'s for protection against histamine were calculated by probit analysis. In this test the $ED_{50}$ indicates that at that particular dose 50% of the animals were completely protected against histamine challenge at the time of testing (1 hour post-dosing). Complete protection was defined as no histamine symptoms for six minutes in the aerosol chamber (approximately 10× the collapse time of the control animals).

TABLE II

Results of In Vivo Antihistamine Assays

| Compound[a] | $ED_{50}$[b](mg/kg,p.o.) 4 hr post dosing |
| --- | --- |
| Doxepin (E:Z = 4:1) | >>9 |
| Z-2-$CO_2H$ (1) | 0.15 |

[a]The purity of these compounds was in excess of 96%
[b]The number of animals was at least 40

In addition to these results, it was found that Compound 1 could provide very long durations of antihistamic activity.

EXAMPLE G

Anaphylactoid Activity

Non-fasted, Wister rats (180–300 g) were dosed with the test compound (i.p. or p.o.) 2 hours before compound 48/80 challenge. One hour prior to challenge, 5 mg/kg i.p. of propranolol was administered. The anaphylactoid inducing agent, compound 48/80 which is well known in the art of pharmacology, was given intravenously at 2 mg/kg and the animals were monitored for symptoms of respiratory distress. Data were analyzed by Probit determinations. The response was quantitated by determining the dose of test compound which protected 50% of the animals from death at a given time point.

The above experimental design does not give positive results for selective antihistamines. Also rats do not respond to histamine (i.v.) with symptoms of anaphylaxis. Agents which block the effects of compound 48/80 are commonly classified as inhibitors of anaphylactic mediators or inhibitors of the release of anaphylic mediators.

TABLE III

Inhibition of Compound 48/80 Induced Anaphylactoid Reaction

| Compound | $ED_{50}^{a,b}$ |
|---|---|
| Triprolidine | >30 |
| Doxepin | 0.15 |
| $\underline{Z}$-2-$CO_2H$ (1) | 1.1 |

[a] Dose of compound (p.o.) providing 50% protection against death induced by compound 48/80.
[b] At least 50 animals were used in each assay.

Compound 1 (example 1) had an approximately $LD_{50}$ in rats of 210 mg/kg (i.p.) and greater than 500 mg/kg (p.o.).

EXAMPLE 8

Formulations

The active compound is (Z)-11-(3-(dimethylamino)-propylidene)-6,11-dihydrodibenz[b,e]oxepin-2-carboxylic acid, i.e., Compound 1.

| (A)-Injection | |
|---|---|
| Ingredient | Amount per ampoule |
| Active Compound | 1.0 mg |
| Water for Injections, q.s. | 1.0 mL |

The finely ground active compound is dissolved in the water for Injections. The solution is filtered and sterilized autoclaving.

| (B)-Suppository | |
|---|---|
| Ingredient | Amount per suppository |
| Active Compound | 1.0 mg |
| Cocoa Butter or Wecobee ™ Base q.s. | 2.0 g |

Wecobee is a trademark and is a hydrogented fatty carboxylic acid.

The finely ground active compound is mixed with the melted suppository base (either Cocoa Butter or Wecobee ™ base), poured into moulds and allowed to cool to afford the desired suppositories.

| (C)-Syrup | |
|---|---|
| Ingredient | Amount per mL |
| Active Compound | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Colouring | q.s. |
| Water | Q.S. to 5.0 mL |

Ethanol, sucrose, sodium benzoate, methylparaben, and flavouring are combined in 70% of the total batch quantity of water. Colouring and the active compound are dissolved in the remaining water, then the two solutions are mixed and clarified by filtration.

| (D)-Tablet | |
|---|---|
| Ingredient | Amount per Tablet |
| Active Compound | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound is finely ground and intimately mixed with the powdered excipients lactose, corn starch, potato starch and magnesium stearate. The formulation is then compressed to afford a tablet weighing 126 mg.

| (E)-Capsule | |
|---|---|
| Ingredient | Amount per Capsule |
| Active Compound | 1.0 mg |
| Lactose | 440.0 mg |
| Magnesium Stearate | 5.0 mg |

The finely ground active compound was mixed with the powdered excipients lactose and magnesium stearate and packed into gelatin capsules.

| (F)-Tablet | |
|---|---|
| Ingredient | Amount per Tablet |
| Active Compound | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet is prepared from the above formulation by the method previously described in example 7 (D)

| (G)-Syrup | |
|---|---|
| Ingredient | Amount per 5 mL |
| Active Compound | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavour | q.s. |
| Glycerol | 500 mg |
| Sucrose | 2000 mg |
| Purified Water q.s. to | 5.0 mL |

A syrup containing other active ingredients in addition to a compound of formula (I) is prepared from the above ingredients by an analogous method to that described for Example 7 (C) above.

| (H)-Nasal Spray | |
|---|---|
| Ingredient | Amount per 100.0 mL |
| Active Compound | 1 g |
| Sodium Chloride | 0.8 g |
| Preservative | 0.5 g |
| Purified Water q.s. | 100.0 mL |

The preservative is dissolved in warm purified water and after cooling to 25°–30° C. the sodium chloride and the compound of formula (I) are added. The pH is then adjusted to 5.5–6.5 and purified water is added to bring the final volume to 100.0 mL.

| (I)-Ophthalmic Solution | |
|---|---|
| Ingredient | Amount per 100.0 mL |
| Active Compound | 0.1 g |
| Sodium Chloride | 0.8 g |
| Preservative | 0.5 g |
| Water for Injection q.s. | 100.0 mL |

This formulation is prepared in a similar way to the nasal spray.

| (J)-Topical Cream | |
|---|---|
| Ingredient | Amount per 100.0 g |
| Active Compound | 0.1 g |
| Emulsifying Wax, N.F. | 15.0 g |
| Mineral Oil | 5.0 g |
| White Petrolatum | 5.0 g |
| Preservative | 0.25 g |
| Purified Water q.s. | 100.0 g |

The preservative is dissolved in approximately 50 g of warm purified water and after cooling to about 25°–30° C. the compound of formula (I) is added. In a separate container the emulsifying wax, mineral oil and white petrolatum are mixed well and heated to approximately 70°–80° C. The aqueous solution containing the compound of formula (I) is added to the warm mixture of emulsifying wax, mineral oil and petrolatum with vigorous mixing while cooling to 25° C. Additional purified water is added with mixing to bring the total weight of the cream to 100.0 g.

We claim:

1. A compound of formula (I)

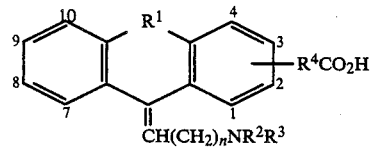

or a pharmacologically and pharmaceutically acceptable salt thereof; wherein $R^1$ is —$CH_2$—O—, $R^2$ and $R^3$ are the same or different and are each hydrogen or $C_{1-4}$ alkyl, $R^4$ is a $C_{1-2}$ bivalent hydrocarbon group and is joined to the aromatic ring system at the 2 position and n is 2.

2. The compound of claim 1 in which $R^2$ and $R^3$ are methyl.

3. The compound of claim 1 which is (z-11-(3-(Dimethylamino)propylidene)-6,11-dihydrodibenz[b,e]oxepin-2-acrylic acid.

* * * * *